(12) United States Patent
Harrison et al.

(10) Patent No.: US 6,670,501 B1
(45) Date of Patent: Dec. 30, 2003

(54) PROCESS FOR THE PRODUCTION OF METHYL METHACRYLATE

(75) Inventors: Stephen Patrick Harrison, Yarm (GB); William David Parten, Nr. Stokesley (GB); Joseph Youngblood Stuart, Baton Rouge, LA (US); John Stuart Martin, Northwich (GB)

(73) Assignee: Lucite International UK Limited, Southampton (GB)

( * ) Notice: Subject to any disclaimer, the term of this patent is extended or adjusted under 35 U.S.C. 154(b) by 0 days.

(21) Appl. No.: 09/462,669

(22) PCT Filed: Jul. 10, 1998

(86) PCT No.: PCT/GB98/02028
§ 371 (c)(1),
(2), (4) Date: Apr. 6, 2000

(87) PCT Pub. No.: WO99/02481
PCT Pub. Date: Jan. 21, 1999

(30) Foreign Application Priority Data

Jul. 12, 1997 (GB) ............................................... 9714632

(51) Int. Cl.⁷ ............................................... C07C 67/48
(52) U.S. Cl. ................... 560/218; 560/205; 562/599; 562/600
(58) Field of Search ................ 560/218, 205; 562/600, 599

(56) References Cited

U.S. PATENT DOCUMENTS

| | | | |
|---|---|---|---|
| 3,440,276 A | | 4/1969 | Wolf et al. |
| T0,955,005 I4 | * | 2/1977 | Stutler et al. ............... 560/218 |
| 4,230,888 A | * | 10/1980 | Paspek et al. ............... 210/721 |
| 5,504,247 A | * | 4/1996 | Saxer et al. ................ 562/600 |
| 6,380,427 B1 | * | 4/2002 | Miyazaki et al. ........... 562/600 |

FOREIGN PATENT DOCUMENTS

| | | | |
|---|---|---|---|
| DE | 10003497 A1 | * 4/2001 | ............ C07C/57/07 |
| EP | 06161998 A1 | * 3/1994 | ............ C07C/57/04 |
| EP | 686647 A1 | * 12/1995 | ............. C08F/4/46 |
| EP | 1078669 A1 | * 2/2001 | ............ B01D/9/00 |
| GB | 1107234 | 3/1958 | |
| GB | 1235208 | 6/1971 | |
| JP | 408134139 A | * 5/1996 | ......... C08F/120/14 |

OTHER PUBLICATIONS

Hawley's "Condensed Chemical Dictionary", 13–th Edition, John Wiley & SOns, Inc, pp. 742 and 931.*

* cited by examiner

Primary Examiner—Tatyana Zalukaeva
(74) Attorney, Agent, or Firm—Pillsbury Winthrop LLP

(57) ABSTRACT

A process for the manufacture of methyl methacrylate includes a process for separating the methyl methacrylate from certain impurities, at least one of which has a freezing point of greater than −50° C., by a fractional crystallisation process.

15 Claims, No Drawings

PROCESS FOR THE PRODUCTION OF METHYL METHACRYLATE

This application is the national phase of international application PCT/GB98/02028 filed Jul. 10, 1998 which designated the U.S.

The present invention relates to a process for the production of methyl methacrylate.

Conventionally, methyl methacrylate has been produced industrially by the well known acetone-cyanohydrin route. The process is capital intensive and produces methyl methacrylate at a relatively high cost.

Other processes for the production of methyl methacrylate are disclosed in U.S. Pat. No. 3,535,371, U.S. Pat. No. 4,336,403, GB-A-1107234, JP-A-63002951 in which propionic acid or its methyl ester is reacted with formaldehyde or derivatives in the presence of methanol. However, there is no disclosure in these references of how to separate the methyl methacrylate product from the residual reactants, and other by-products of the reaction with which it is associated.

One problem which is encountered in the separation of the methyl methacrylate product from such reactions is that the by-products produced, for example methyl isobutyrate and diethyl ketone, are difficult to separate from the methyl methacrylate by conventional distillation methods because their boiling points are very similar. The boiling point of methyl methacrylate at atmospheric pressure is 100° C., whilst that of methyl isobutyrate is 92° C. and diethyl ketone is 100° C. The molecules are also similar in size and shape so that separation by means of molecular sieves offers little potential. There is therefore a need for a process to produce methyl methacrylate which overcomes the above-described problem of separating the methyl methacrylate product from certain impurities.

GB-A-1235208 describes a process for the purification of alkyl methacrylates which are contaminated with impurities which have melting points below −50° C., especially methyl isobutyrate and lower alkyl iodides, by fractional crystallisation and counter-current washing of the resulting methyl methacrylate crystals. This document, however, does not indicate any suitable process for the removal of impurities from methyl methacrylate which have melting points above −50° C.

Two of the principal impurities found in a quenched product stream of a condensation reaction between formaldehyde and methyl propionate are diethyl ketone (DEK) and methyl isobutyrate (MIB). Whilst MIB has a melting point of −85° C., DEK has a melting point of −39° C., which is higher than that of methyl methacrylate at −47° C. We have now found that MIB, DEK and other compounds may be removed from methyl methacrylate by fractional crystallisation.

Accordingly the present invention provides a process for the production of methyl methacrylate, which process comprises the steps of:
(i) reacting propionic acid or an ester thereof with formaldehyde or a precursor thereto in a condensation reaction to produce a gaseous product stream comprising methyl methacrylate, residual reactants, methanol and byproducts;
(ii) processing at least a portion of the gaseous product stream to form a liquid product stream comprising substantially all of the methyl methacrylate and at least one impurity which melts at a temperature of greater than −50° C.; and subjecting said liquid product stream to at least one fractional crystallisation stage which comprises the steps of:

(iii) cooling said liquid product stream to between about −45° C. and about −95° C. such that said liquid product stream forms crystals of solid methyl methacrylate and mother liquor, said crystals containing a higher proportion of methyl methacrylate than does said liquid product stream or mother liquor,
(iv) separating said crystals of solid methyl methacrylate from said mother liquor and
(v) melting said crystals to form liquid methyl methacrylate which contains a lower concentration of said impurities than said liquid product stream.

In this way, substantially pure methyl methacrylate may be obtained from a complex product stream which contains a range of impurities having a range of melting points falling both above and below that of the pure methyl methacrylate.

The methyl methacrylate recovered from the process preferably contains less than 0.5% by weight of other materials, more preferably less than 0.2% by weight, and especially less than 0.1% by weight of undesirable impurities.

Preferably the methyl methacrylate is produced by the condensation of methyl propionate with formaldehyde or a precursor thereto, e.g. methylal, and particularly by the condensation of methyl propionate with formaldehyde. By-products from the reaction include water, diethyl ketone (DEK), propionic acid (PA), methacrylic acid (MAA) and methyl isobutyrate (MIB) and methanol.

The condensation reaction is preferably conducted in the presence of a catalyst, e.g. a caesium catalyst on a silica support. The condensation reaction stage may be conducted at any suitable temperature and pressure. Typically, the condensation reaction stage is conducted at a temperature from 250 to 400° C. and preferably from 300 to 375° C. Typically, the condensation reaction stage is conducted at a pressure from $10^4$ to $10^6$ N.m$^{-2}$ and preferably from $10^5$ to $10^6$ N.m$^{-2}$.

The gaseous product stream from the condensation reaction may be liquefied by any suitable means, e.g. quenching, condensing. The resulting liquid stream is then separated into a liquid product stream and one or more streams containing residual materials by means of e.g. fractional distillation. Any residual feed materials recovered are preferably recycled to the condensation reaction.

The liquid product stream may comprise up to 20% by weight of materials such as MIB and DEK (3-pentanone), PA or MM produced by side reactions. The liquid product stream preferably contains less than 20%, more preferably less than 5% of such impurities. The level of impurities or by-products may be controllable by adjusting the reaction conditions or post-reaction separations.

The liquid product stream is cooled to between about −45° C. and about −95° C. so that a part of the liquid product stream freezes to form crystals of solid methyl methacrylate and a mother liquor or supernatant, which is that part of the liquid product stream which remains unfrozen.

The level of impurities in the methyl methacrylate crystals may be affected by the rate at which the liquid product stream is cooled. The rate at which the liquid product stream is cooled may be controlled to optimise the separation of the methyl methacrylate from the impurities by minimising the amount of impurities contained in the crystals. A relatively slow rate of cooling has been found to produce methyl methacrylate crystals which contain a lower proportion of impurity than crystals formed as a result of faster cooling of the liquid product stream. The rate of cooling of the liquid product stream is preferably less than 30° C./min, more preferably less than 20° C./min and most preferably less than 10° C./min. A lower rate of cooling may be preferable, e.g. less than 5° C./min.

The crystals of methyl methacrylate which form on cooling the liquid product stream may be further treated to remove residual mother liquor, e.g. by washing or sweating. The crystals may be washed with a suitable solvent to remove the residual mother liquor and dried. The crystals of methyl methacrylate may be partially melted or "sweated" to reduce impurities. By partially melting the crystals, the impure portions of the crystal which melt at a lower temperature than the pure material may be removed. This process also encourages the release of any small amounts of mother liquor which may have become encapsulated in the crystals during their formation or which remains at the surface of the crystals.

The mother liquor which remains after the methyl methacrylate crystals have been removed may be further purified, e.g. by a further crystallisation process to increase the yield of purified methyl methacrylate.

The liquid methyl methacrylate obtained from the fractional crystallisation process may be further purified by a further fractional crystallisation process. Several crystallisation stages may be required, depending on the final product purity required. Preferably the process includes between one and six successive crystallisation stages. The design of crystallisation processes which include multiple crystallisation stages is well known to those skilled in the art. The crystallisation process may be performed using known equipment for such processes including batch, scraped wall and falling film crystallisers, the design of which would be determined by the nature and scale of the process to be accommodated.

The crystallisation process is particularly suitable for separating methyl methacrylate from a liquid stream which contains components which have boiling points very close to that of methyl methacrylate. In particular MIB and/or DEK may be present in a methyl methacrylate stream as described above.

The invention therefore also provides a method for separating methyl methacrylate from a liquid mixture comprising methyl methacrylate and up to 20% of a liquid impurity having a melting point above −50° C., comprising the steps of:

(i) cooling said liquid mixture to between about −45° C. and about −95° C. such that said liquid mixture forms crystals of solid methyl methacrylate and mother liquor, said crystals containing higher proportion of methyl methacrylate than does said liquid mixture or mother liquor, (ii) separating said crystals of solid methyl methacrylate from said mother liquor and (iii) melting said crystals to form liquid methyl methacrylate which contains a lower concentration of said impurity than said liquid mixture.

The liquid methyl methacrylate product may be further purified by successive further crystallisation steps as described above.

The methyl methacrylate produced by the process of the invention is useful in the manufacture of polymethyl methacrylate and a variety of acrylic copolymers which have a very large number of applications.

Illustrative examples of the invention are described below.

EXAMPLES 1–3

The purification of MMA by successive fractional crystallisation stages was studied for three initial compositions of MMA/DEK mixtures.

Mixtures having the initial mixture compositions of 20%, 1% and 0.25% v/v of DEK in MMA were made up. Each mixture was then placed in a boiling tube fitted with a stirrer which was placed in a methanol/solid carbon dioxide bath and cooled rapidly for about two minutes until crystals were formed. The temperature at this point was recorded to be between −55° C. and −62° C. The mother liquor was removed and the crystals were washed three times with methanol and then dried under vacuum. The crystals were allowed to melt and a sample of the melt was analysed using gas chromatography. The procedure was repeated starting from the melt formed in the previous stage. The results are shown in Table 1. The results indicate that by successive crystallisation of MMA containing 0.25% v/v DEK, the DEK level may be reduced to about 600 ppm.

TABLE 1

|  | Example 1 | Example 2 | Example 3 |
| --- | --- | --- | --- |
| Initial mixture composition DEK in MMA | 20% v/v | 1% v/v | 0.25% v/v |
|  | % v/v DEK in melted crystal | | |
| 1st crystal | 15.43 | 0.56 | 0.25 |
| 2nd crystal | 12.10 | 0.43 | 0.15 |
| 3rd crystal | 8.76 | 0.34 | 0.13 |
| 4th crystal | 4.15 | 0.19 | 0.06 |
| 5th crystal | 0.41 | | |

EXAMPLE 4

The effect of the rate of cooling on the composition of the resulting MMA crystal has been studied. A sample of MMA containing 1% v/v DEK was split into two portions. The first portion was cooled rapidly using the technique described in Examples 1–3. The second portion was cooled more slowly using a series of methanol/acetone/water/solid carbon dioxide baths of intermediate temperatures such that cooling was acheived over a period of thirty minutes. The rate of cooling therefore was approximately 2° C./min. The results are shown in Table 2.

TABLE 2

|  | Dek % V/V | |
| --- | --- | --- |
|  | Liquor | Crystal |
| Original Soln | 1.00 | |
| Rapid Cooling | 1.13 | 0.53 |
| Slow Cooling | 1.32 | 0.25 |

EXAMPLE 5

A mixture of MMA with other components was prepared and cooled slowly in a methanol, water and Drikold bath having a temperature of approximately −65° C. Cuboid crystals formed at a temperature of −54.8° C. The supernatent liquor was removed by filtration and the crystals were washed with cold methanol and filtered again. The methanol was removed by vacuum and the crystals allowed to thaw. The mass of the crystals was 32g and the mass of the supernatent liquor was 17g. The composition of the crystals and of the liquor was determined by titraton (for acids) and gas chromatography (for the other components). The results and initial composition are shown in Table 3.

The results show that the level of a number of impurities in a methyl methacrylate mixture can be reduced by a fractional crystallisation method even when the mixture contains a range of impurities which have a melting point which is higher than that of methyl methacrylate itself.

TABLE 3

| COM-PONENT | M. pt (° C.) | feed mixture (wt %) | Crystals at −54.8° C. (wt %) | Liquor at −54.8° C. (wt %) |
|---|---|---|---|---|
| MMA | −48 | 98.97 | 99.54 | 97.94 |
| MAA | 16 | 0.15 | 0.03 | 0.44 |
| PA | −21 | 0.33 | 0.12 | 0.61 |
| DEK | −39 | 0.32 | 0.18 | 0.62 |
| MIB | −85 | 0.23 | 0.13 | 0.39 |

What is claimed is:

1. A process for the production of methyl methacrylate, which process comprises the steps of:
   (i) reacting propionic acid or an ester thereof with formaldehyde or a precursor thereto in a condensation reaction to produce a gaseous product stream comprising methyl methacrylate, residual reactant, methanol and byproducts;
   (ii) processing at least a portion of the gaseous product stream to form a liquid product stream comprising substantially all of the methyl methacrylate and at least one impurity which melts at a temperature greater than that of methyl methacrylate;
and subjecting said liquid product stream to at least one fractional crystallisation stage which comprises the steps of:
   (a) cooling said liquid product stream to between the freezing temperature of methyl methacrylate and about −95° C. such that said liquid product stream forms crystals of solid methyl methacrylate and mother liquor, said crystals containing a higher proportion of methyl methacrylate than does said liquid product stream or mother liquor,
   (b) separating said crystals of solid methyl methacrylate from said mother liquor and
   (c) melting said crystals to form liquid methyl methacrylate which contains a lower concentration of said at least one impurity than said liquid product stream.

2. A process as claimed in claim 1, wherein said at least one impurity which melts at a temperature of greater than −50° C. comprises diethyl ketone, methacrylic acid and/or propionic acid.

3. A process as claimed in claim 1, wherein the liquid product stream is cooled at a rate of less than 30° C. per minute.

4. A method for separating methyl methacrylate from a liquid mixture comprising methyl methacrylate and at least one impurity which melts at a temperature greater than that of methyl methacrylate, comprising the steps of:
   (a) cooling said liquid product stream to between the freezing temperature of methyl methacrylate and about −95° C. such that said liquid product stream forms crystals of solid methyl methacrylate and mother liquor, said crystals containing a higher proportion of methyl methacrylate than does said liquid product stream or mother liquor,
   (b) separating said crystals of solid methyl methacrylate from said mother liquor and
   (c) melting said crystals to form liquid methyl methacrylate which contains a lower concentration of said at least one impurity than said liquid product stream.

5. A method as claimed in claim 4, wherein between one and six successive crystallisation stages are used.

6. A process as claimed in claim 1, wherein between one and six successive crystallization stages are used.

7. A process as claimed in claim 2, wherein between one and six successive crystallization stages are used.

8. A process as claimed in claim 3, wherein between one and six successive crystallization stages are used.

9. A process as claimed in claim 1, wherein the liquid product stream is cooled at a rate of less than 20° C. per minute.

10. A process as claimed in claim 1, wherein the liquid product stream is cooled at a rate of less than 10° C. per minute.

11. A process as claimed in claim 1, wherein the liquid product stream is cooled at a rate of less than 5° C. per minute.

12. A process as claimed in claim 2, wherein the liquid product stream is cooled at a rate of less than 30° C. per minute.

13. A process as claimed in claim 2, wherein the liquid product stream is cooled at a rate of less than 20° C. per minute.

14. A process as claimed in claim 2, wherein the liquid product stream is cooled at a rate of less than 10° C. per minute.

15. A process as claimed in claim 2, wherein the liquid product stream is cooled at a rate of less than 5° C. per minute.

* * * * *